United States Patent von Schuckmann

[11] Patent Number: 6,056,728
[45] Date of Patent: May 2, 2000

[54] DEVICE FOR DISPENSING DISCRETE DOSES OF A LIQUID

[75] Inventor: Alfred von Schuckmann, Kevelaer, Germany

[73] Assignee: Rhone- Poulenc Rorer Arzneimittel GmbH, Koln, Germany

[21] Appl. No.: 08/932,145

[22] PCT Filed: Feb. 3, 1997

[86] PCT No.: PCT/EP97/00469

§ 371 Date: Sep. 29, 1998

§ 102(e) Date: Sep. 29, 1998

[87] PCT Pub. No.: WO97/29797

PCT Pub. Date: Aug. 21, 1997

[30] Foreign Application Priority Data

Feb. 12, 1996 [DE] Germany .......................... 196 04 838

[51] Int. Cl.[7] .................................................. A61M 5/00
[52] U.S. Cl. ...................... 604/207; 604/135; 604/157; 604/231
[58] Field of Search .................................... 604/135, 136, 604/156, 157, 191, 207, 226, 231

[56] References Cited

U.S. PATENT DOCUMENTS

| | | | |
|---|---|---|---|
| 4,755,169 | 7/1988 | Sarnoff et al. .............................. | 604/51 |
| 5,092,843 | 3/1992 | Monroe et al. .......................... | 604/138 |
| 5,298,023 | 3/1994 | Haber et al. .............................. | 604/90 |
| 5,456,672 | 10/1995 | Diederich et al. ...................... | 604/226 |
| 5,749,968 | 5/1998 | Melanson et al. ...................... | 118/300 |

FOREIGN PATENT DOCUMENTS

| | | |
|---|---|---|
| 1 491 841 | 11/1965 | Germany . |
| 2 106 338 | 9/1971 | Germany . |
| 2 187 962 | 9/1987 | United Kingdom . |

*Primary Examiner*—Corrine McDermott
*Attorney, Agent, or Firm*—Proskauer Rose LLP

[57] ABSTRACT

The invention is directed to a device (V) for the output of a liquid (2) in partitioned amounts (2') from a store room (3), preferably in form of a cartridge (K), over an output mouth piece (4), preferably in form of an injection needle (5), and has the object the application of exactly reproducible amounts from a reserve amount and its safe application. This is obtained by an intermediate reservoir (17) taking up the partitioned amount (2') from the store room (3), whereby for the intermediate reservoir (17) an output piston (19) is provided with a penetration canal (18) to fill the intermediate reservoir (17).

22 Claims, 5 Drawing Sheets

DEVICE FOR DISPENSING DISCRETE DOSES OF A LIQUID

BACKGROUND OF THE INVENTION

The invention is directed to a device for the output of a liquid in partitioned amounts out of a store region, preferably in the form of a cartridge, via an output mouth piece, preferably in the form of a attached injection needle.

Injection means of this sort are well known, disclosed for example, in the form of bar-shaped devices (U.S. Pat. No. 2,591,457) or in the form of inoculation pistols (U.S. Pat. No. 2,472,116). Such devices comprise a spring hammer, the strokes of which are controllable. This spring hammer is arranged in the back side of a charge chamber in which a conventionally shaped syringe can be installed. Depending on the stroke distance of the spring hammer that can be lockably adjusted in positions, the piston of the syringe is shifted in the direction of the output mouth piece. Such a gradual output finally leads to a total evacuation. The syringe is then generally thrown away.

The object of the invention is to provide a device of the above type that partitions, in a simple way, reproducible amounts coming out of a store region and to make them easily applicable.

SUMMARY OF THE INVENTION

This object is realised by the invention mentioned in the claims.

By such a development a device of the according type with a higher value of use is obtained. First of all this is achieved by a intermediate reservoir taking up the partitioned amount from the store room, whereby the intermediate reservoir comprises an output piston with a penetration canal to fill the intermediate reservoir. The amount to be drained is drawn from the back side of the piston to its front side and separated strictly from the remaining reserves. The inventive device no longer requires expenditure of great effort over the whole filling length, as was heretofore the case for known syringes. Accordingly, anologously functioning mechanical conditions are provided which can be adjusted in an optimum way to the parameters of an injection needle/liquid. Moreover this has the advantage that the reserve is held in readiness in a less expensive package. The syringe functioning in a certain way also as packing is surely too expensive to throw it away. It is furthermore advantageous if the output piston is movable, together with the receiver containing the store region, by filling the intermediate reservoir and when the output piston cylinder forming the intermediate reservoir is shiftable, together with this receiver, into the opposite direction. This produces on one hand a clear charging stroke in one direction and on the other hand an injection stroke into the opposite direction. In order to avoid a backwards movement when the output pressure is produced, an advantageous measure is taken that provides a stop valve between the store region and the intermediate reservoir. It is moreover advantageous that the shifting movement take place in the opposite direction and in successive phases. In this way an advancing stroke that brings the injection needle, and respectively the hollow needle, into a guiding position can be realized in addition to the injection stroke. The hollow needle projects out of a cover. The injection stroke occurs in an appropriate way only in the last moment, so that, before that the phases run constantly. The release is very abrupt and is based in both cases on a release of a spring being charged in a manner appropriately effecting the operation. Another advantage is that the cylinder continues in a sleeve surrounding the receiver. Both parts guide each other and they mutually provide stability, so that the device can be produced with thin walls. This leads to a reduction of the weight and permits in addition a relatively compact structural shape. The inventive device can literally be shaped with the dimensions of a cigarette package. With respect to another advantageous arrangement of the parts of the device, the invention proposes to arrange both springs at the upper end, i.e. meaning the end on the opposite side of the output mouth piece, of the sleeve/receiver and to be supported by an outer casing. The aimed stable shifting, and respectively guiding, of the receiver in the sleeve is supported by the corresponding coaxial adjustment in respect to the receiver. In order to generate the reserves, and respectively to obtain a simple refilling possibility, it is proposed that the outer casing comprise a charge inlet arranged concentrically to the store room of the receiver. A further development of this is characterized in that the charge inlet is closed by a plug whereby impeccable sterility can be obtained. The plug can have a function surpassing the corresponding closing function in that way such as it has a length that leads to an appropriate docking of the cartridge. The device can only be charged with plugs. The cartridge can be easily put in. When the charging stroke is realized the flow connection is directed to the penetration canal, which provides the advantage that the docking only occurs when the device is conditioned. The cartridge is appropriately formed as a glass carpule. The device is furthermore characterized in that a common release button is provided to release the spring effect. This makes the operation of such an injection means much more easy, whereby it is particularly advantageous that the release button is formed at an arm of the release lever having two arms which is arranged in such a way that it directly releases a support of the sleeve, whereby the sleeve itself comprises an abutment for the support of the receiver. This abutment is driven into the released position by docking at the supporting structural component of the sleeve. The supporting structural component is conveniently in the form of a bar being charged with springs in the effective direction and arranged at the other arm of the release lever having two arms. The back side of the bar forms the corresponding control bevel. Conditioned by the fact that the release lever extends in parallel with the unit of the sleeve/receiver in the outer casing of the device, the length required of the outer casing is thus impeccably exhausted. Another solution being particularly suitable is characterized in that the sleeve can be moved back, together with the receiver, into the position submitted to the spring tension by a handle, preferably a protecting cap that can be moved up from the mouth piece, whereby the sleeve drags along the receiver into an intermediate position from which the receiver can then be moved into the position submitted to the spring tension by operating a shiftable cocking lever. Alternatively, the charging stroke and the subjecting to tension of the energy reservoir could also be accomplished by operating the shiftable cocking lever. For this purpose it is further operated in such a way that the shiftable cocking lever is arranged within a longitudinal slot of the sleeve, whereby this longitudinal slot forms a stopper for the drag movement at its upper edge. A further embodiment is characterized in that the spring of the receiver provides greater tension than the spring of the sleeve. Finally a further advantageous development is characterized in that a cover surrounding the mouth piece and comprising an annular room to let the wall of the handle, respectively the protecting cap, enter, whereby the entering is limited by the stopper. In this way a small hand driven injection means is obtained in an easy to handle form and one very suitable for the stress of use. It can also be recharged very quickly and it supplies exactly reproducible amounts.

The object of the invention is explained in detail by an example illustrated by a drawing, in which like reference numerals designate the same elements:

DETAILED DESCRIPTION OF THE PREFERRED EMBODIMENT

The device V, formed as injection means, comprises an essentially rectangular, flat outer casing 1 and serves for the output of exactly reproducible amounts 2' of a liquid 2 kept ready in a store room (region) 3.

The liquid 2 can be a drug, as for example for the postoperative treatment of patients. The application is realized by an output mouth piece 4. Successively to this an injection needle 5 supported by a so-called Luer-connection 6 is arranged, the screw thread flanks 7 of which threadably engage a threaded counter-piece 8 in the top section 9 of the device V.

The threaded counter-piece 8 is formed in an inner side at the annular wall 10 surrounding the bottom of the output piece 4 extending conically outward. The injection needle 5, and respectively the hollow needle, is arranged in a sleeve-shaped base 11 which is funneled in its inner side in a corresponding counter-conical way to the walling of the output mouth piece 4. Such configuration assures an impeccable sealed closure. The tapering degree is relatively low.

An exchangeable cartridge K represents the store room 3, whereby this cartridge K is a so called glass carpule which is opened at its bottom side and that comprises a tracking piston 12 moving with increasing output of the liquid 2 in the direction of a shaft 13 of the cartridge K and stopping before an inner shoulder 14 of the cartridge K. The outlet following with respect to the output direction is closed by a piercable sheet gasket 15 which is fixed by means of a bordering cap 16 consisting of metal foil. The central pierce section of such a liquid source can be exposed in a known way. The bordering cap 16 is fixed at the shaft-sided bottom edge of a beaded part of the shaft 13.

The amount 2' of the liquid 2, i.e. the amount 2' to be separated and originating from the mentioned source, is supplied to the output mouth piece 4 over an intermediate reservoir 17 limiting the corresponding output volume, where the amount 2' is moved to the destination by means of the injection needle 5. A central penetration canal 18 forms the corresponding flow bridge.

The intermediate reservoir 17 comprises an output piston 19 which is guided within a cylinder 20. The cylinder 20 forms the extension of the annular wall 10 of the output mouth piece 4, whereby the extension is directed towards the inner side of the casing.

Figure 3:
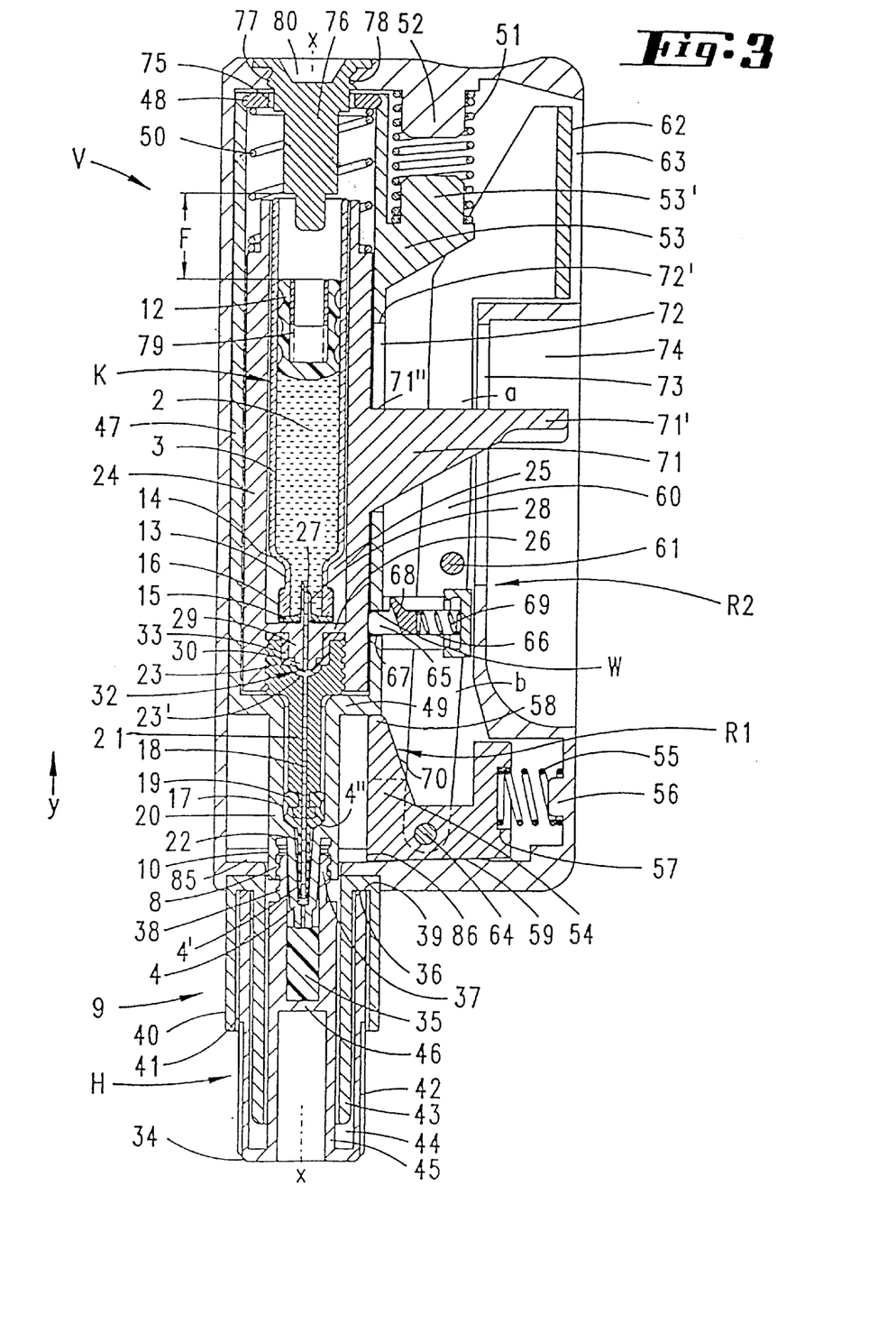
FIG. 3 is a vertical sectional view of the device shown, closed and not charged (showing the situation according to FIG. 1)

As shown, for example, in FIG. 3 penetration canal 18 extends over the whole length of the piston shaft 21 as well as over the section of the output piston 19 itself and then further continues in a central pipe socket 22. The pipe socket 22 rises clearly above the front surface of the output piston 19, the front surface being the surface facing the intermediate reservoir. In the closed, non-charged position as well as in the injection position, the pipe socket 22, the side walls of which taper in the direction of the free end thereof, projects into a shape-corresponding pointed cavity section 4' of the output mouth piece 4. In the injection position the separated amount 2" is thus completely drained out of the intermediate reservoir 17, by virtually particularly of the fact that the front surface of the output piston 19 has, in the intermediate section of the cylindrical section of the cylinder 20 in the direction of the pointed section, an appropriate shape 4" correspondingly to the shoulder.

The end section of the piston shaft 21 nearest the store room 3 comprises a screw socket 23. The outer screw thread of the screw socket 23 threadably engages an appropriate inner screw thread of a pot-shaped receiver 24, the pot cavity 25 of which can, as already mentioned, be directly used as store room 3 simply by putting in a cartridge K or correspondingly indirectly, whereby in the store room 3, precautions are taken for an impeccable and hygienical uptake of the liquid 2.

For the flow connection to the penetration canal 18, a bottom-forming transverse wall 26 of the receiver 24 is broken through in the central section. The transverse wall 26 separates the pot cavity 25 into a longer room on the side of the reserves and a shorter room on the side of the output mouth piece. The screw socket 23 is arranged in the shorter room. The transverse wall 26 leaves a connecting canal 27 open. Its section protruding into the pot cavity 25, and which is arranged on the side of the reserves, is provided in the form of a sharpened hollow needle 28 which is a part of a docking device, the counter-part of which is the above mentioned piercable sheet gasket 15. The piercing position of the bordering cap 16, being correspondingly opened in the central section, is clearly shown in the drawing.

On the side of the intermediate reservoir the transverse wall 26 continues in a cylindrical projection 29 (see FIG. 7) which ends with a semi-spherical dome 30 being in distance from the border. The end of the connecting canal 27 runs into the zenith of the dome 30.

Figures 6, 7:
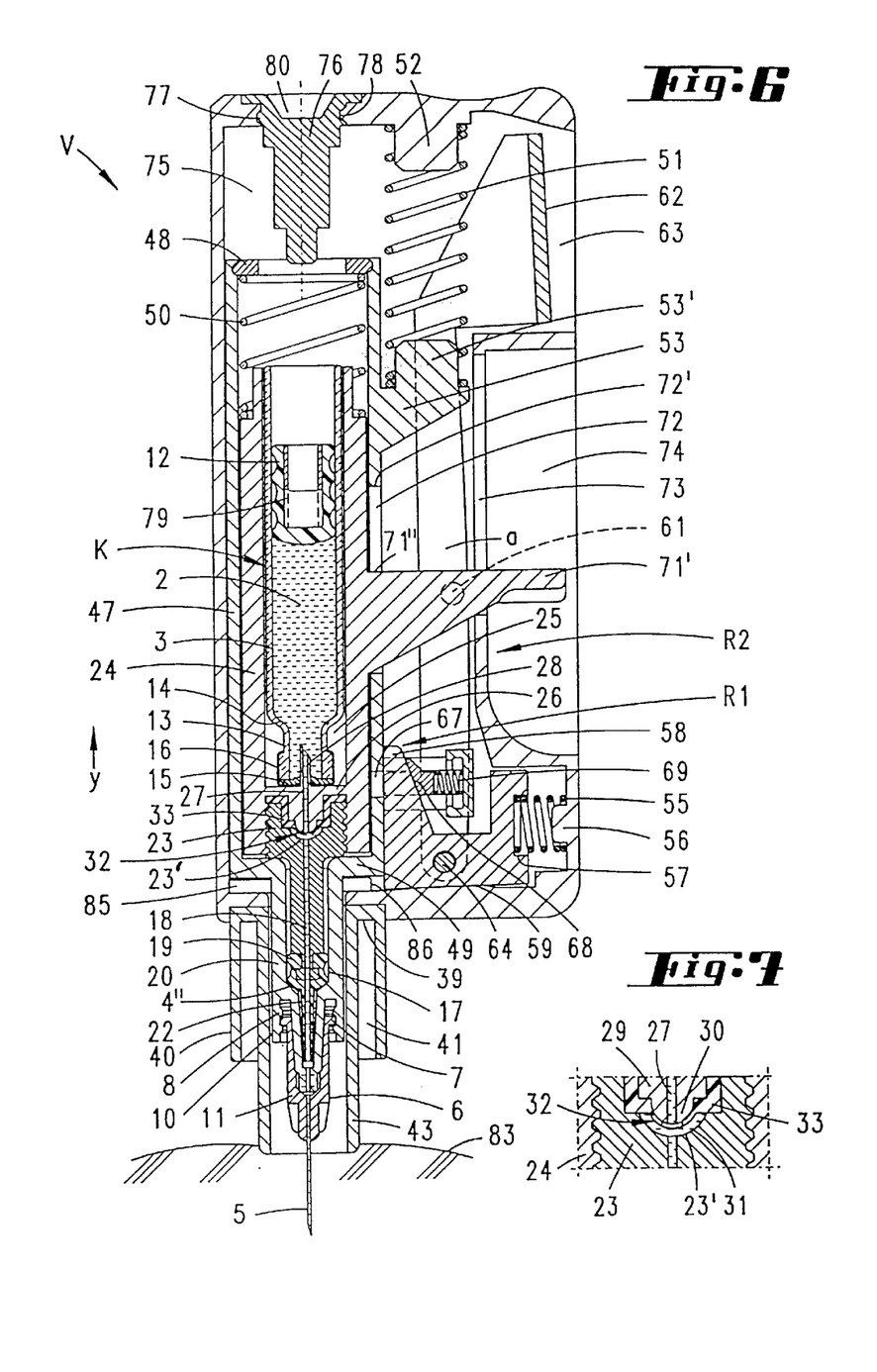
FIG. 6 is a vertical sectional view of the device during, and respectively after, the realization of the injection.
FIG. 7 is an enlargement of the stop valve arranged between the store region and the intermediate reservoir.

The dome 30 carries a correspondingly vaulted wall section 31 that forms a stop valve 32, provided, for example, as a slot valve. The edge of the dome-shaped, vaulted wall section 31 rests in a hat-shaped sealing insert 33 between the gradually vaulted front surface of the screw socket 23 and the unit projection/dome 29/30 forming a counter-profile.

The receiver joint is correspondingly configured. The sealing insert 33 consists of rubber, respectively rubber-elastic material. Space is left in front of the wall section on the side of the screw socket.

The output piston 19 consists of the same above mentioned material. The output piston 19 is arranged correspondingly shaped on a fungiformed projection of the piston shaft 21 and includes the usual piston rings.

The intermediate reservoir 17 is charged by a displacement of the output piston 19 in the direction of the store room 3 in such a manner that a negative pressure is generated in the cylinder 20, the negative pressure leading to the taking up of the liquid 2 via the flow bridge 27, 18, 22. The slot edge of the wall section 31 can, depending on the opening, emerge slightly from the dome 30 because of the shape-adjusted and thus semi-spherical concave cavity 23' of the screw socket 23, the cavity 23' functioning also as intermediate chamber.

A suction of unwanted air over the output mouth piece 4 is avoided by a sealing protection cap 34, which contains a sealing body 35 (see FIG. 3) sealing the opening end of the corresponding canal section.

The protection cap 34 functions concurrently as charging handle H of the device V, which can be coupled with the cylinder 20 over the Luer-connection 6. Changing handle H furthermore comprises screw thread rails 38 being adequate to the screw thread flanks 7 at a nozzle-shaped projection 37 protruding above the front edge 36 of the pot-shaped protection cap 34, whereby the screw thread rails 38 can also be realized in the form of a continuous multi-threaded steep angle thread. The latter ones threadably engage a threaded counter-part 8. The screw/seal position is exactly defined in a manner such that the mentioned front edge 36 hits a casing-sided stopper 39 which is arranged within a pot-shaped cover 40. The opening of this cover 40 is directed into the opposite direction of the outer casing 1, whereas the opening of the protection cap 34 is arranged vice-versa. The stopper position is shown in FIG. 3. The handle H immerses with cover 40 over about the half of its length.

In order to increase the grip, the free-standing mantle wall section, i.e. the part that does not immerse into the annular room 41 of cover 40, is roughened, particularly being longitudinally fluted. The flutes are designated with the reference number 42. The pot-shaped cover 40 comprises a central ring connection piece 43 which protrudes over beyond the free end of the cover. The ring connection piece 43 presents a diameter of such dimensions that the ring wall 10, and respectively the cylinder 20 having the same diameter, can be axially moved within it. The ring connection piece 43 fits into a counter ring room 44 of the double-walled protection cap 34. The seal body 35 located at an inner ring wall 45 is supported by a transverse wall 46 of the ring wall.

On the side of the store room 3 the cylinder 20 continues in sleeve 47 which surrounds the receiver 24 being axially guided therein and limited by a stopper. The stopper at the ending of sleeve 47 forms a latched ring plate 48. The store room-sided stopper is realised by a ring shoulder 49 defined by a wall displacement between cylinder 20 having a smaller diameter and the cylindrical sleeve 47 having a three times larger diameter.

Both axially movable parts 24 and 47 are submitted to the same spring loading. Both springs 50 and 51 are arranged at the upper edge, meaning i.e. the edge located opposite to outlet the direction of the liquid 2, of the receiver 24 and the sleeve 47. These springs are thread pressure springs. The spring 50 of the receiver 24 is attached to a shoulder-forming offset end section of the receiver 24 and is located with its outer spring winding at the inner side of the ring plate 48. The spring 50 operates on the longitudinal middle axis x—x of the device V, meaning that it is situated concentrically to the coaxial lining of the liquid bridges and the piston displacements.

In addition to this internal spring-biased support of the receiver 24, the embracing and guiding sleeve 47 is supported itself by the other mentioned spring 51 which again is supported by the section of the outer casing 1. It is mounted onto a stump 52 forming a fixed spring bearing. A corresponding stump 53' starts from an extension arm 53 of the sleeve 47. It forms a movable spring bearing and supports this end of the spring 51. The middle axis of the stumps 52, 53' extends in parallel with the longitudinal middle axis x—x.

The springs 50, 51 can be arranged under initial tension.

The position submitted to the spring tension is maintained by self-latching lockings R1 and R2. The locking R1 maintains the spring loaded position of sleeve 47. This locking R1 comprises a supporting structural component 54 in the form of a bar being shiftable crosswise to the longitudinal middle axis x—x. This bar is biased with spring tension in the direction of the locking. The spring providing such biasing is designated with the numeral 55 and operates in the back side of the mentioned bar. It is supported in a stable manner at its casing-sided end winding by the outer casing 1. In this regard, a stump 56 also fixes the position. The bar-sided end winding is located in a dell 57. A nose 58 forms the actual support-active part. It is located underneath the sleeve 47 forming with its bottom side, together with a blocking shoulder, a ring shoulder 49. The supporting structural component 54 is based on slide surface 59 formed by the inner side of the outer casing 1.

The release of the locking R1 is implemented by a release lever 60 having two arms and being located in pivotable position around an axle end 61 in the interior of the outer casing 1. Its arm a continues in a release button 62 being arranged in a deepening 63 accessible from the outside and protected from incidental contact. The deepening 63 is located at the end of the outer casing 1, the end being situated opposite to the injection needle 5. The release button 62 is as large as a finger tip. Moreover the release button 62 covers the device parts being located behind it, as for example the spring 51 etc., so that they cannot be seen.

The release lever 60 starting in one piece at the back side of the release button 62 extends through the outer casing 1 of the device V mainly running parallel to the side of the unit of the sleeve/receiver 47/24. Thereby the other arm b of the release lever 60 protrudes into the section of the supporting structural component 54. There, it is connected with the supporting structural component 54 via a link pin 64. A loading of the release button 62 in the direction of the arrow P (FIG. 4) is converted into a movement releasing the locking function R1, i.e. the nose 48 is removed from underneath the ring shoulder 49, so that the sleeve 47 submitted to the spring tension projects together with the receiver 24 being in a chargeable position.

The release lever 60 releases the support of the sleeve 47 directly over the supporting structural component 54, i.e. rather indirectly (when the intermediate component 54 is not considered), whereas the receiver 24 is released from the spring tension directly by the locking R2, whereby the sleeve 47 forms an abutment W for the corresponding support of the receiver 24 in the sleeve 47. This is realized by a blocking piece 65 which is arranged in a guidance 66. The guiding direction is situated crosswise to the longitudinal middle axis x—x of the unit receiver/sleeve 24/47. A control bevel 68 is located outside the mantle surface of the sleeve 47, the control bevel 68 being a connection to the pivot-like part of the blocking piece 65, the pivot-like part clearing a breakthrough 67 of the sleeve 47 walls and forming with its free inner end the actual abutment W relative to the receiver 24. The blocking piece 65 is subjected to a spring 69 tensioned in the direction of the blocking position, whereby the spring 69 is supported by the end of a transverse console forming the guidance 66.

The control bevel 68 with its sharp angle is directed to the longitudinal middle axis x—x in such a manner that the nose 58 of the supporting structural component 54 can be inserted from the bottom side of the central bevel 68 when the locking R1 is released, as shown in FIG. 6. Consequently the receiver 24 is released, whereby the receiver 24 then is displaced relative to the sleeve 47 by the pressure of the spring 50. As a result, the amount 2' located in the intermediate reservoir 17 is injected.

The control bevel 68 operates together with the back side of the nose 58 functioning as correspondingly transverse control counter surface 70.

The receiver 24 continues in a crosswise extending shiftable cocking lever 71 by which the receiver 24 can be displaced relative to the sleeve 47 against the tension of the spring 50. The shiftable cocking lever 71 extends over a longitudinal slot 72 of the wall of the sleeve 47. The usable length of the longitudinal slot 72 corresponds to the displacement stroke between the receiver 24 and the sleeve 47.

The free end of the shiftable cocking lever 71 further extends through an opening 73 of the outer casing 1. The end 71' of the shiftable cocking lever 71 forms an operating handle. The end 71' runs into a gripping dell 74 of the device V and does not protrude into the exterior. This avoids incidental, undesired releases.

The shiftable cocking lever 71 forms with its bottom-sided upper edge 71" a stopper for the coupled motion, whereby the sleeve-like counter-part of the stopper is the upper end 72' of the longitudinal slot 72.

It is to be noted that the outer casing 1 comprises a fill inlet 75 located concentrically to the store room 3, and respectively to the pot cavity 25 of the receiver 24. This inlet 75 is closed by a plug which is designated with the number 76. It comprises a thread 77 in its wide, stopping head section, respectively socket section, whereby the thread 77 with a corresponding counter thread is arranged in a thread bore 78 of the outer casing 1, the thread bore 78 being situated congruently to the fill inlet 75. The plug 76 penetrates with its thinner zone the opening of the ring plate 48 in order to protrude with its sectionally further thinner zone into the cylindrical cavity of the cartridge K. A last and third, again reduced zone enters a central cavity of the tracking piston 12 which is stiffened by an adequately measured bearing bush 79.

Figures 4, 5:
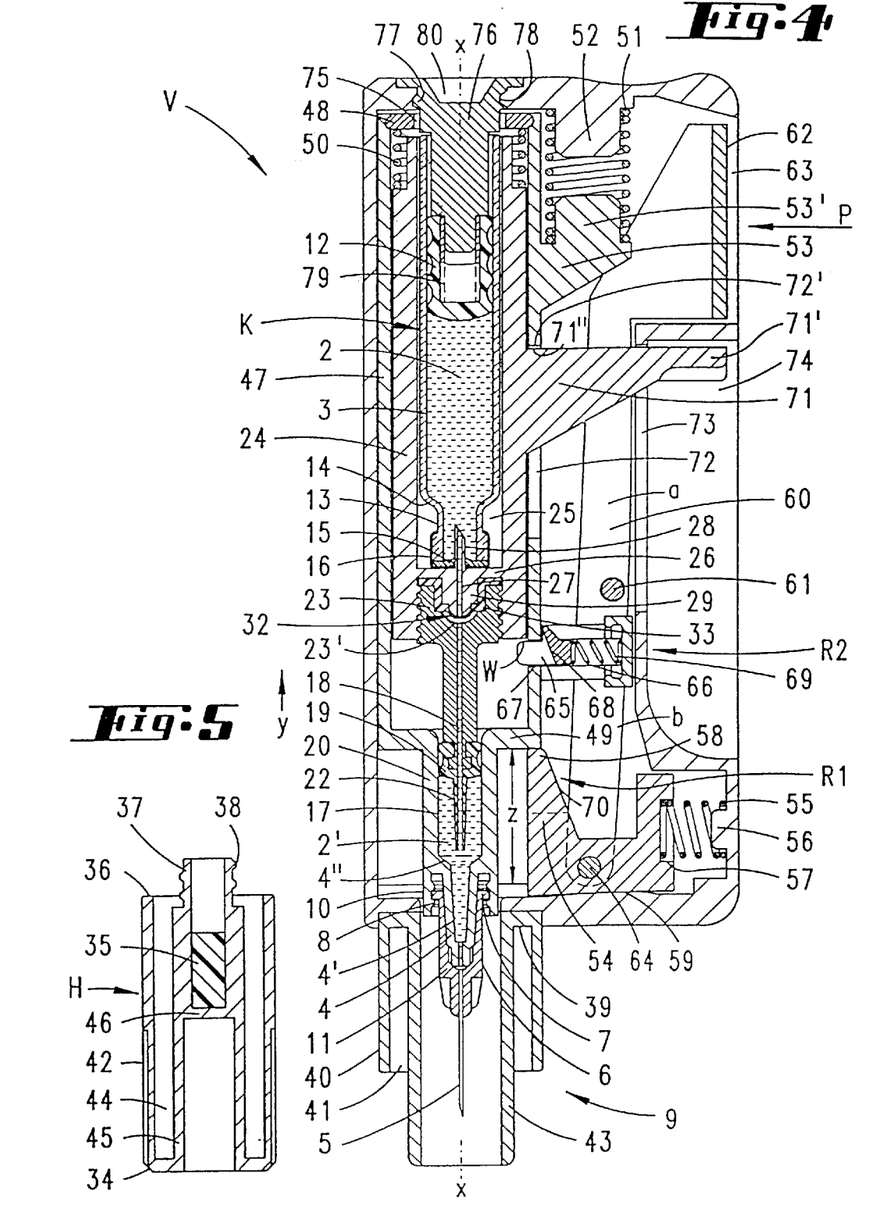
FIG. 4 is a vertical sectional view of the charged device.
FIG. 5 is a vertical sectional view through the removed handle.

As FIG. 4 shows, the plug 76 has a length leading to an appropriate docking of the cartridge K, whereby, however, an axial free floating F (FIG. 3) is considered that at least mainly corresponds respectively to the level length of the hollow needle 28. The cartridge K is only then supplied to the connecting canal 27 and to the successive penetration canal 18 when the device V is charged, i.e. meaning when the partition of the amount 2' in the intermediate reservoir 17 takes place.

Figure 1:
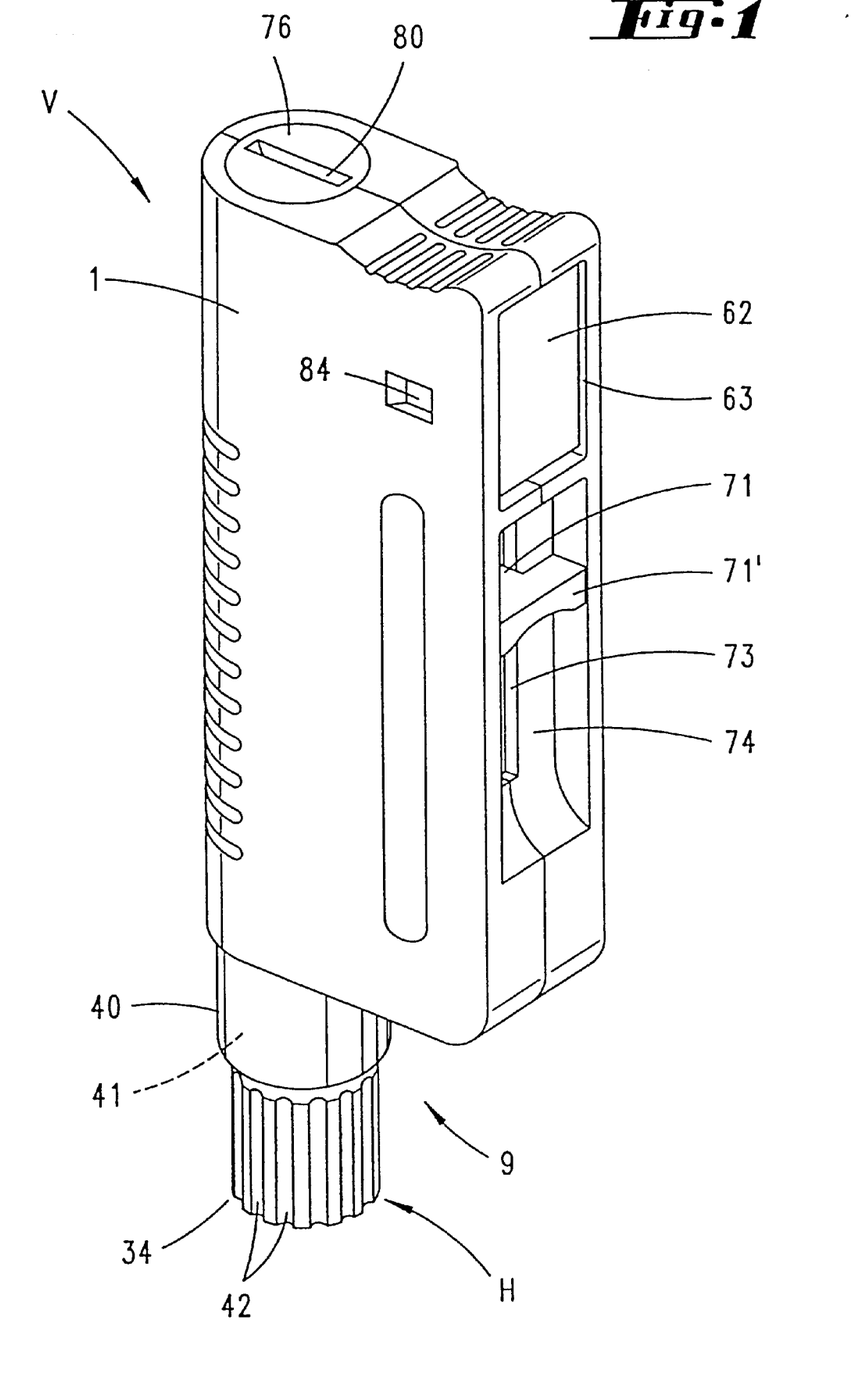
FIG. 1 is a perspective view, of the inventive device shown closed and still not charged.
Figure 2:
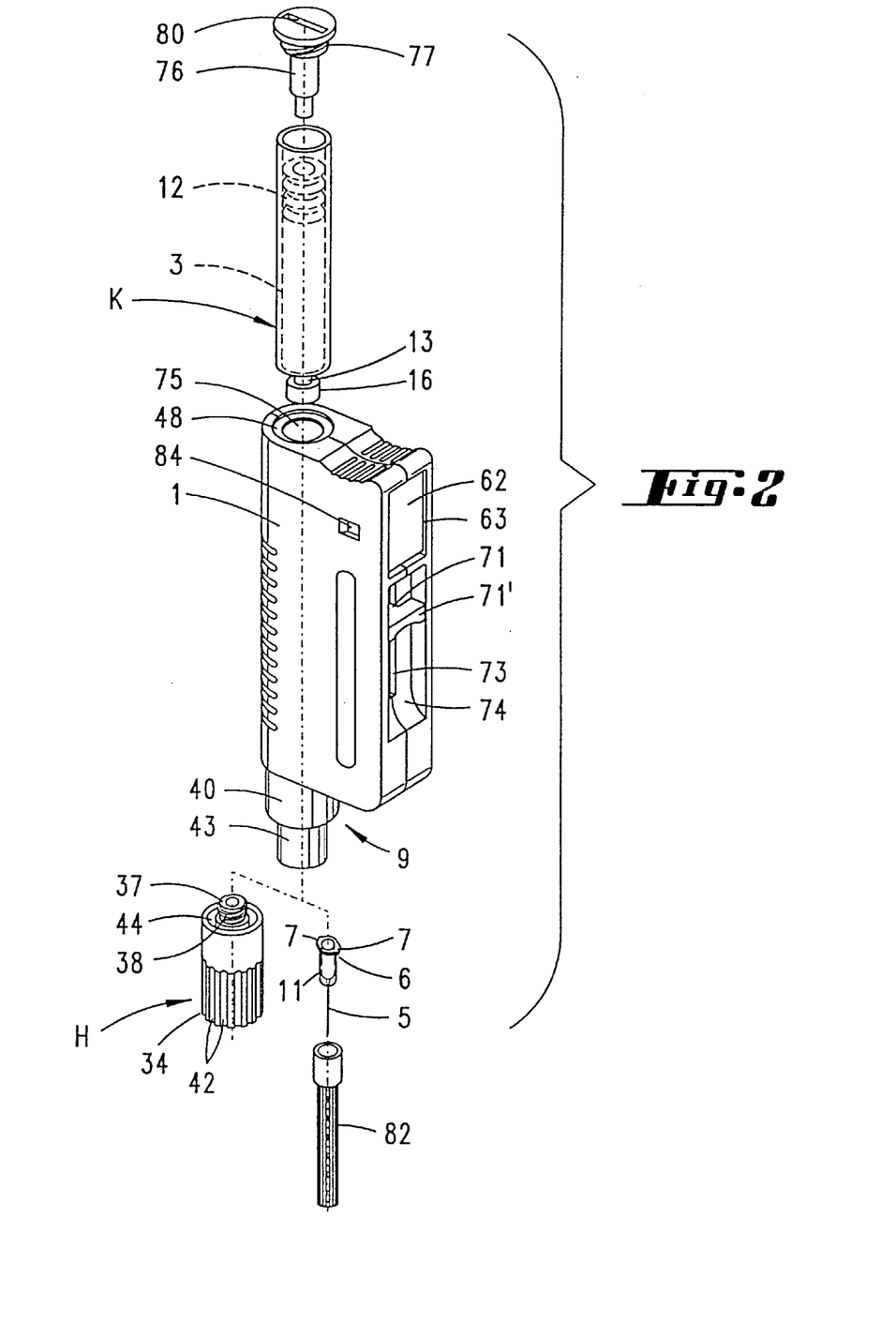
FIG. 2 is an exploded view of the device, depicting a changing of the cartridge, removed handle, as well as view of a hollow needle with a separated hollow needle protection.

The function of the device V is now described, as follows. By opening the store room 3 the cartridge K is arranged. The plug 76 can be operated threadwise by a gripping slot 80, as for example with a coin. The insertion of the cartridge K is described in FIG. 2. The docking position shown in FIG. 3 can be carried out at the very beginning by a particularly advantageous surpassing of the mentioned axial free floating F in such a manner that the cartridge K is inserted completely into the pot cavity 25 and that the plug 76 is added. The use of the axial free floating F provides the advantage that the flow bridge is realized only when the device is used, i.e. when then injection needle 5 is provided.

In order to achieve the ready-to-charge position, the cylinder 20 protruding, from the outer casing 1 for example, because of a previous use, is displaced against the loading of the spring 51, into the interior of the outer casing 1, by using the handle H, i.e. the protection cap 34. By using the Luer-connection 6 the appropriate operating connection can be obtained over the screw thread rails 38. The input direction is designated with y. During this displacement, the spring 50 maintains the output piston 19 in its leading position. The bar-like supporting structural component 54 latches, by forming the locking R1, under the ring shoulder 49. This is the non-charged, closed intermediate position as it is shown in FIG. 3.

From this point the charging of the intermediate reservoir 17 can be carried out which is implemented by a relative displacement of the receiver 24 to the sleeve 47. This is achieved by further moving the shiftable cocking lever 71 in the direction of the arrow y against the resistance (tension) of spring 50. This is carried out until the position subjected to the spring tension according to FIG. 4 is achieved. By achieving this position the device V is charged. During this operation the output piston 19 was recognizably displaced within the cylinder 20 in the direction of the arrow y. The negative pressure (partial vacuum) emerging hereby sucks the amount 2' to be exactly applied into the intermediate reservoir 17. It is thus supplied from behind the output piston 19 before the front surface forming a pressure bottom. The stop valve 32 controls this afflux. Unwanted air is not sucked up, since the seal body 35 blocks the opening of the canal section of the output mouth piece 4.

In order to administer the separated amount 2', the handle H is removed and the injection needle 5, respectively the hollow needle, is fixed over the Luer-connection 6. This is carried out without contaminations by using a plug handle 82 being available on the trade market and taking up the injection needle 5 in a sterile way. Corresponding dragging projections are located between the socket part 11 of the Luer-connection 6 and the inner walls of the plug handle 82.

Via the locking R2 in the position subjected to the spring tension the receiver 24 is supported by the abutment W being effective therein.

Now the injection can be carried out. Such action is initiated when the release button 62 is pressed. The release lever 60 moves against the tension of the spring 55 which, after the release, brings the release lever 60 back into the locking position. The spring 55 functions at the same time as a restoring spring. By pressing the button, a displacement of the supporting structural component 54 away from the sleeve 47 is effected. The sleeve 47 loses its support by the nose 58 and quickly moves downwards in the opposite direction of the arrow y. The injection needle 5 thereby emerges from the protecting cover 40 so that it is then freely situated above the central ring nozzle 43 and penetrates into the application area 83 of a patient or other subject. In this way a rapid subcutaneous or intramuscular injection is obtained.

In the end phase of this downward movement caused by the spring, the blocking piece 65 forming on the part of the locking R2 comes into the effective section of the control counter-surface 70 of the supporting structural component 54. This situation is shown in FIG. 6. The abutment W is thus receded from the support-active projection located opposite to the bottom side of the receiver 24. The spring 50 presses the output piston 19 in the opposite direction of the arrow y. The separated amount 2' is completely applied since, despite the emerging output overpressure caused by the effect of the stop valve 32, nothing can flow back into the store room 3.

Altogether, the device thus functions in a manner such that the output piston 19, together with its receiver 24 containing the store room 3, is firstly displaced upwardly under filling the intermediate reservoir 17, meaning under effectuating a charging stroke in the direction of the arrow y, and that, by a corresponding release, the cylinder 20 of the output piston 19, the cylinder 20 forming the intermediate reservoir 17, is then displaced, together with this receiver 24, in the opposite direction of the arrow y. This opposite stroke, i.e. the shifting movement in the opposite direction of the arrow y, takes place in successive time phases, whereby this shifting movement consists of an advancing stroke removing the injection needle 5 from underneath the cover 40 and an injection stroke. In the beginning the time phases take place simultaneously, whereas in the end phase a subsequent injection stroke takes place.

It is particularly advantageous for the handling that the two time phases are set on by the release button 62 by correspondingly releasing the spring effects.

The recharging is possible only when the injection needle 5 was removed since its length does not permit an arrangement of the handle (H) in the way that a displacement of the cylinder 20, the displacement causing a complete spring charging stroke z, could be realized. Moreover the Luer-connection 6 is occupied by the screw thread flank 7. This forcibly leads to the fact that a new needle has to be attached. The injection means can thus be applied by each person.

In special, reliable cases it could be advantageous to conduct the spring charging stroke z immediately via the shiftable cocking lever 71. In this case, the spring 50 of the receiver 24 is set under higher tension than the spring 51 of the sleeve 47. In this regard the end 72' of the longitudinal slot 72 is used as dragging stopper. The relatively more "supple" spring mainly subsides.

The content of the glass carpule is provided with about ten amounts 2' to be separated into equal parts. The released charges can be optically measured by a numerator device 84 which is located in one of the large areas of the device V.

In its lower end position the ring shoulder 49 comes in contact with the correspondingly lengthened glide surface 59 or, as shown, with a rail 85 that surpasses the ring shoulder 49 in that way that it is slightly directed to the inside of the sleeve, whereby the front surface of the rail 85 being situated on the side of the supporting structural component 54 forms a locking stopper 86 for the supporting structural component 54.

All the disclosed characteristics are significant for the invention. For this purpose, the content of the disclosure of the adequate/enclosed priority documents (copy of the prior application) is completely included into the disclosure of the application, whereby the aim of this is to integrate the characteristics of these documents in the claims of the present application.

I claim:

1. A device for the output of a liquid in partitioned amounts, comprising:
   a receiver;
   a store room receivable in the receiver for containing a supply of the liquid;
   a cylinder including structure defining an intermediate reservoir for containing the partitioned amount when transferred from the store room;
   an output mouth piece for delivery of the partitioned amount from the intermediate reservoir; and
   an output piston movable within the intermediate reservoir, the output piston including a penetration canal for transfer of liquid from the store room to the intermediate reservoir, the output piston being movable together with the receiver in a first direction, movement of the output piston and the receiver relative to the intermediate reservoir in the first direction filing the intermediate reservoir with the partitioned amount of liquid from the store room when same is received in the receiver, the cylinder and the receiver each being movable in a second direction opposite to said first direction.

2. The device according to claim 1, wherein the output mouth piece includes an injection needle.

3. The device according to claim 1, further comprising a reflux valve disposed between the store room and the intermediate reservoir.

4. The device according to claim 1, further comprising a mechanism for imparting movement to the cylinder and the receiver in the second direction in successive phases.

5. The device according to claim 4, wherein the mechanism for imparting movement includes two springs for respectively biasing the cylinder and the receiver, the successive phases being implemented by releasing the two springs held in a loaded condition.

6. The device according to claim 5, wherein the cylinder continues in a sleeve surrounding the receiver.

7. The device according to claim 6, further comprising an outer casing, one of the springs being arranged at the top end of the sleeve and the other of the springs being arranged at the top of the receiver, both of the springs being supported by the outer casing.

8. The device according to claim 7, further comprising a release mechanism for releasing the two springs, the release mechanism including a common release button.

9. The device according to claim 8, wherein the release mechanism further includes a release lever having two arms, the release button being arranged at one of the arms.

10. The device according to claim 9, wherein the release mechanism further includes a support for engaging the sleeve and preventing movement of the sleeve in the second direction when engaged therewith, the release lever directly releasing the support from engagement with the sleeve, the sleeve including an abutment for supporting the receiver prior to movement thereof to a released position, the abutment being driven into the released position in response to docking thereof on the support following disengagement of the support from the sleeve.

11. The device according to claim 10, wherein the support includes a bar loaded with the springs in the second direction, the bar being arranged at a remaining arm of the release lever.

12. The device according to claim 9, wherein the release lever extends in the outer casing of the device parallel with the receiver and the sleeve.

13. The device according to claim 7, further comprising:
   a handle for urging the sleeve together with the receiver in the first direction into an intermediate position in which the sleeve is subjected to spring tension; and
   a shiftable cocking lever for further urging the receiver from the intermediate position in the first direction into another position in which the receiver is subjected to spring tension.

14. The device according to claim 13, wherein the handle is a protecting cap that can be moved up from the mouth piece.

15. The device according to claim 14, wherein the sleeve includes a longitudinal slot, the shiftable cocking lever being arranged within the longitudinal slot, the longitudinal slot forming a stop at an upper edge thereof for engaging an upper edge of the shiftable cocking lever when the receiver is moved into said another position.

16. The device according to claim 14, further comprising a cover surrounding the mouth piece, the cover including an annular room in which a wall of the protecting cap is receivable to an extent limited by structure of the cover defining a stop within the annular room.

17. The device according to claim 7, wherein the spring of the receiver is more tensioned than the spring of the sleeve.

18. The device according to claim 1, further comprising an outer casing including a filling inlet arranged concentrically to a cavity formed in the receiver corresponding to the store room.

19. The device according to claim 18, further comprising a plug for closing the filling inlet.

20. The device according to claim 19, wherein the store room is a cartridge.

21. The device according to claim 20 wherein the cartridge is a glass carpule.

22. The device according to claim 20, wherein the plug has a length that effects an appropriate docking of the cartridge within the receiver when the plug is positioned to close the filling inlet.

* * * * *